(12) United States Patent
Weisshaupt et al.

(10) Patent No.: US 8,177,804 B2
(45) Date of Patent: May 15, 2012

(54) SURGICAL INSTRUMENT

(75) Inventors: Dieter Weisshaupt, Immendingen (DE);
Anton Keller, Duerbheim (DE);
Christoph Rothweiler, Donaueschingen (DE)

(73) Assignee: Aesculap AG, Tuttlingen (DE)

( * ) Notice: Subject to any disclaimer, the term of this patent is extended or adjusted under 35 U.S.C. 154(b) by 818 days.

(21) Appl. No.: 12/287,384

(22) Filed: Oct. 7, 2008

(65) Prior Publication Data
US 2009/0112246 A1  Apr. 30, 2009

(30) Foreign Application Priority Data

Oct. 30, 2007 (DE) .................. 10 2007 053 359

(51) Int. Cl.
*A61B 17/32* (2006.01)

(52) U.S. Cl. ........................ 606/174; 606/51

(58) Field of Classification Search ............. 606/51, 606/52, 170, 171, 205, 206, 45, 167, 174
See application file for complete search history.

(56) References Cited

U.S. PATENT DOCUMENTS

| 6,174,309 | B1 * | 1/2001 | Wrublewski et al. ........... 606/45 |
| 6,514,252 | B2 * | 2/2003 | Nezhat et al. ................... 606/48 |
| 6,676,660 | B2 * | 1/2004 | Wampler et al. ................ 606/51 |
| 6,743,230 | B2   | 6/2004 | Lutze et al. |
| 2002/0111624 | A1 | 8/2002 | Witt et al. |
| 2006/0079891 | A1 * | 4/2006 | Arts et al. ....................... 606/51 |

FOREIGN PATENT DOCUMENTS

| DE | 20 2006 016 837 | 1/2007 |
| DE | 20 2007 005 510 | 6/2007 |
| EP | 1 250 102       | 10/2002 |
| EP | 1 810 625       | 7/2007 |

* cited by examiner

*Primary Examiner* — Victor Nguyen
(74) *Attorney, Agent, or Firm* — Lipsitz & McAllister, LLC

(57) ABSTRACT

A surgical instrument with a clamping device for holding and/or clamping tissue, a severing device for severing tissue and a handling device for actuating the clamping device and/or the severing device is provided. The clamping device is provided with at least one clamping member having a clamping surface and a clamping member opening. The severing device is provided with a severing member movable at least partially into the clamping member opening. In order to reliably prevent short circuits between the at least one clamping member and the severing member, a severing member guide device is provided for guiding the severing member in the clamping member opening and for maintaining a spacing from inner side surfaces of the clamping member opening.

46 Claims, 3 Drawing Sheets

SURGICAL INSTRUMENT

CROSS-REFERENCE TO RELATED APPLICATIONS

The present disclosure relates to the subject matter disclosed in German application number 10 2007 053 359.6 of Oct. 30, 2007, which is incorporated herein by reference in its entirety and for all purposes.

FIELD OF THE INVENTION

The present invention relates to a surgical clamping and severing instrument generally, and more specifically to a surgical instrument comprising a clamping device for holding and/or clamping tissue, a severing device for severing tissue and a handling device for actuating the clamping device and/or the severing device, the clamping device comprising at least one clamping member having a clamping surface and a clamping member opening, and the severing device comprising a severing member movable at least partially into the clamping member opening.

BACKGROUND OF THE INVENTION

A surgical instrument of the kind described at the outset is known, for example, from U.S. Pat. No. 6,174,309 B1. This is a scissors-like instrument which unites the functions of scissors and a clamp. In particular, when suitable conductive contacts are provided on at least one clamping member and/or on the severing member, such an instrument can be used for grasping and for severing tissue with simultaneous coagulation of the tissue. It is, therefore, suited, in particular, for performing two steps to be taken during surgery, namely the severing and the coagulating, in a single step, with the tissue to be severed being able to be held with the instrument before, during and after the severing.

A disadvantage of the known instruments is, however, that the severing member may come into contact in an undesirable manner with the clamping member, thereby causing a short circuit, in particular, when both the at least one clamping member and the severing member are connected to a power supply unit, for example, a high-frequency generator, when inserting the severing member into the clamping member opening. Such short circuits are, however, undesired, as they may result in burning of the tissue accompanied by strong carbonization. Also, tissue may thus undesirably adhere or become stuck to the electrically conductive surfaces of the instrument and thereby increase their resistance.

Therefore, it would be desirable to provide an instrument of the kind described at the outset which reliably prevents short circuits between the at least one clamping member and the severing member.

SUMMARY OF THE INVENTION

In accordance with the invention, a surgical instrument comprising a clamping device for holding and/or clamping tissue, a severing device for severing tissue and a handling device for actuating the clamping device and/or the severing device is designed such that the clamping device comprises at least one clamping member having a clamping surface and a clamping member opening. Furthermore, the severing device comprises a severing member movable at least partially into the clamping member opening. A severing member guide device is provided for guiding the severing member in the clamping member opening and for maintaining a spacing from inner side surface of the clamping member opening.

BRIEF DESCRIPTION OF THE DRAWING FIGURES

The foregoing summary and the following description may be better understood in conjunction with the drawing figures, of which:

DETAILED DESCRIPTION OF PREFERRED EMBODIMENTS OF THE INVENTION

Figure 1:
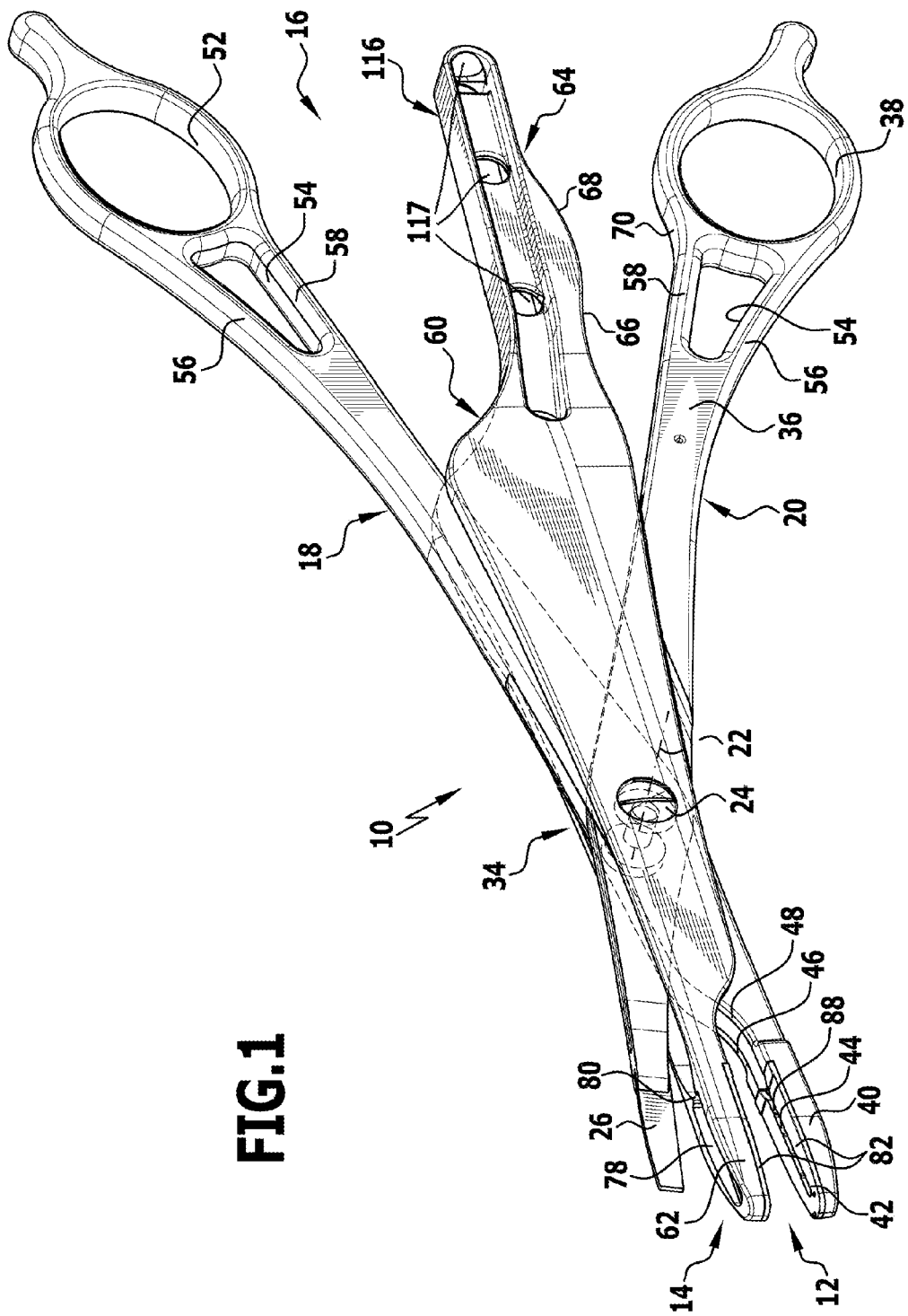
FIG. 1 shows a perspective general view of a surgical instrument.

Although the invention is illustrated and described herein with reference to specific embodiments, the invention is not intended to be limited to the details shown. Rather, various modifications may be made in the details with endoscope and range of equivalents of the claims and without departing from the invention.

The present invention relates to a surgical instrument comprising a clamping device for holding and/or clamping tissue, a severing device for severing tissue and a handling device for actuating the clamping device and/or the severing device, the clamping device comprising at least one clamping member having a clamping surface and a clamping member opening, and the severing device comprising a severing member movable at least partially into the clamping member opening, wherein a severing member guide device is provided for guiding the severing member in the clamping member opening and for maintaining a spacing from inner side surfaces of the clamping member opening.

With the severing member guide device of the instrument it is ensured that the severing member is guided at a reliable spacing from inner side surfaces of the clamping member opening and is thereby held in spaced relation to the side surfaces. Direct contact between the severing member and the side surfaces is thereby eliminated. Indirectly, it is thus also possible to prevent the severing member from coming into contact with a clamping surface, preferably of electrically conductive construction in a monopolar or bipolar instrument, which surrounds the clamping member opening. In this way, short circuits are reliably prevented between the severing member and the clamping surface or inner side surfaces of the clamping member opening. In addition, owing to the severing member guide device a defined minimum spacing can be maintained between the severing member and the clamping surface or the inner side surfaces of the clamping member opening, so that a flow of current cannot exceed a specific value during the coagulating.

The construction of the severing member guide device is particularly simple when it comprises at least one spacer element which defines a minimum spacing between the severing member and an inner side surface of the clamping member opening. It is not absolutely necessary for the spacer element itself to be arranged within or in the area of the clamping member opening. It is, of course, also conceivable to provide the at least one spacer element on the severing member itself, for example, the spacer element could be formed on or attached to the severing member.

It is particularly advantageous for at least two spacer elements to be provided, which define a minimum spacing between the severing member and a respective side surface of the clamping member opening. When the two spacer elements are mutually opposed or are arranged on inner side surfaces of the clamping member opening or are arranged on the severing member so as to face away from each other, they have, in addition, a centering function, which defines the severing member and guides it in a centered manner in the clamping member opening.

It may also be expedient for the at least two spacer elements to be associated with mutually opposed or substantially opposed inner side surfaces of the clamping member opening. In particular, this is to be understood as the spacer elements being able to be arranged on the inner side surfaces and/or on the severing member. In any case, they are then associated with the inner side surfaces in such a way that the severing member is unable to touch these, but rather is held at a spacing specified by the at least two spacer elements.

To construct the surgical instrument in the form of a monopolar or bipolar instrument, it is advantageous for the clamping surface to be electrically conductive. In particular, electrically conductive is to be understood as it being of electrically conductive or very low-impedance construction, i.e., having a correspondingly high electrical conductivity, in order to conduct a coagulation current through body tissue from the clamping surface to the severing member or to a further clamping surface of a further clamping member.

Insertion of the severing member into the clamping member opening is particularly simple when the clamping surface is orientated transversely or substantially transversely to the inner side surfaces of the clamping member opening. In particular, transversely is to be understood as a relative inclination at an angle of between 45° and 135°; the clamping surface and the inner side surfaces preferably extend perpendicularly or almost perpendicularly to one another.

To prevent a current from flowing between the severing member and the clamping surface or the clamping member, it is expedient for the severing member guide device to be made at least partially of an electrically non-conductive material. It can also be said that the severing member guide device is made at least partially of an electrically insulating material.

The at least one spacer element is advantageously made of an electrically non-conductive material, which is electrically insulating. In such a spacer element configuration, it is conceivable for the rest of the severing member guide device to be optionally made of an electrically conductive material.

The severing member guide device can be made in a defined shape in a simple way when it and/or the at least one spacer element are made of a ceramic material. The spacer element or the severing member guide device may thus be made completely of electrically insulating construction. A configuration is, however, also conceivable in which ceramic materials are used, which are partly insulating and partly electrically conductive.

The surgical instrument can be assembled in a simple way from different parts when the severing member guide device is of one-piece construction. In particular, the clamping member may be constructed such that it comprises a severing member guide device receptacle into which the severing member guide device may be inserted when assembling the instrument. For example, the severing member guide device can then be easily and securely connected to the clamping member, for example, by a force and/or positive connection, in particular, by locking, adhesive bonding, soldering or welding.

A particularly compact construction of the instrument or the at least one clamping member is achieved when the severing member guide device has an opening whose inner side surfaces form, at least in sections, the inner side surfaces of the clamping member opening. This severing member guide device thus forms part of the clamping member opening.

The construction of the severing member guide device is particularly simple when it has a plate-shaped section, the one section surface of which forms at least part of the clamping surface of the at least one clamping member. If the plate-shaped section is of electrically non-conductive construction, it may be additionally coated or provided with an electrically conductive layer so as to form an electrically conductive clamping surface.

To form a monopolar or bipolar instrument, it is expedient for the section surface forming at least part of the clamping surface to be of electrically conductive construction. This may achieved by coating or appropriate doping of the material from which the plate-shaped section and its surface are formed.

It is advantageous for the plate-shaped section to have a plate opening which forms part of the clamping member opening. The plate-shaped section may, for example, be of U-shaped construction in a plan view, and, therefore, open at one side, or of closed ring-shaped configuration. The plate opening therefore defines part of the clamping member opening; in particular, the severing member can be inserted through the plate opening into the clamping member opening.

Advantageously, a rim projecting from the plate-shaped section is arranged so as to surround the plate opening, and the one inner or outer surface of the rim forms at least partially the inner side surfaces of the clamping member opening. In this way, the clamping member opening may be entirely or partially delimited by the rim. Depending on the choice of materials from which the clamping member and the severing member guide device are constructed, a small predetermined manufacturing tolerance can thus be maintained.

The construction of the severing member guide device is particularly simple when the rim carries the at least one spacer element.

Advantageously, the spacer element extends over an entire height of the rim. It is, however, also conceivable for the spacer element to extend over only part of the height of the rim. In particular, spacer elements are also conceivable, which, as is were, form only point-shaped projections of the rim and extend away from the rim into the clamping member opening.

To ensure optimum guidance of the severing member in the clamping member opening, it is advantageous for the at least one spacer element to extend up to the clamping surface. In particular, this means that a side surface of the spacer element may lie in a plane with the clamping surface and even form part of it.

In particular, a particularly good guidance is achieved by two respective spacer elements which are mutually opposed to each other forming a spacer element pair. For example, when two spacer elements are arranged or formed on the inner side surfaces, a gap is thereby defined between them, whose width is smaller than a spacing between mutually opposed inner side surfaces of the claming member opening. The spacer element pair could, of course, also be arranged on the severing member, more particularly, with such mutually opposed spacer elements that the spacer elements point in directions opposite to each other.

Advantageously, a number of spacer elements are uniformly distributed over the inner side surfaces. Irrespective of a shape of the spacer elements, a uniform arrangement is advantageous as a particularly good guidance of the severing member is thereby achieved over its entire extent.

The construction of the severing member guide device is particularly simple when the spacer elements are of strip-shaped construction. A spacing between the clamping member and the severing member can thereby be reliably defined and maintained along the entire extent of the spacer elements. These preferably extend parallel to a direction of movement of the severing member and the at least one clamping member relative to each other.

A particularly good guidance of the severing member in the clamping member opening is achieved by the spacer elements extending in a direction transverse or substantially transverse to the clamping surface. In particular, the direction in which the spacer elements extend may be parallel to a direction of movement when the severing member and the at least one clamping member are moved relative to each other.

Preferably, the at least one clamping member opening is a depression formed on the clamping member. For example, a bottom of the depression may thus also form a stop for the severing member and delimit a relative movement of the severing member and the at least one clamping member.

It may, however, also be expedient for the at least one clamping member opening to be a through-opening formed on the clamping member. It is thus possible to even guide the severing member partially through the clamping member opening. In particular, this may prove expedient when two clamping members movable relative to each other are provided, and the severing member is mounted for movement relative to the two clamping members, and when one of the two clamping members exerts a double function, namely forms a clamping member of the clamping device and part of the severing device as well.

Preferably, the severing member is at least partially movable through the at least one clamping member opening. This makes it possible to withdraw the severing member from the clamping member at one side, so that it is not surrounded by a clamping member at all, for example, for cleaning purposes. Furthermore, when the severing member is movable through the clamping member opening, it may, if required, project on the other side of the clamping member, and, in particular, interact with a further clamping member, for example, to form a severing device.

In particular, a particularly simple construction of the clamping device can be achieved by it comprising two clamping members which are mounted for movement relative to each other. In particular, it is advantageous for the two clamping members to be mounted for pivotal movement relative to each other.

Furthermore, a simple construction of the severing device may be achieved, in particular, when it comprises a first clamping member and the severing member, which are movable relative to each other. It should also be noted that in a preferred embodiment of the instrument, one of the two clamping members may be both part of the clamping device and part of the severing device.

Expediently, the first clamping member and the severing member are adapted to be brought into contact with each other for severing tissue in a severing position. For example, this may be achieved by the severing member contacting the clamping surface of the at least one clamping member or being inserted into the clamping member opening of the clamping member.

In accordance with a further preferred embodiment of the invention, it may be further provided that in a working position in which tissue may be clamped and/or held and/or severed with the instrument, a second clamping member surrounds the severing member at least partially, and that, without disassembling the instrument, the severing member and the second clamping member may be brought into a cleaning position in which the second clamping member completely releases the severing member. This embodiment enables particularly easy cleaning of the instrument, more particularly, without having to disassemble it. Accordingly, it may also be transferred to the cleaning position during surgery, for example, by an operator, so that the two clamping members and the severing member no longer engage one another and are freely accessible.

It is particularly easy to clean the instrument when the second clamping member is movable away from the severing member in the direction towards the first clamping member in order to transfer the instrument from the working position to the cleaning position.

Tissue can be severed with the instrument in a simple and reliable way when, in the severing position, the severing member projects beyond the second clamping member in the direction towards the first clamping member. The severing member can thus interact with the first clamping member, for example, by engaging in the clamping member opening.

The construction of the surgical instrument is particularly simple when the first and second clamping members are mounted for pivotal movement relative to each other.

It is also expedient for the severing member and the at least one clamping member to be mounted for pivotal movement relative to each other. It is, for example, also possible to select a common pivot axis for relative pivoting of the severing member and the two clamping members, which further simplifies the construction of the instrument.

In order that tissue will not be inadvertently severed with the surgical instrument, it is expedient when, in any working position with the exception of the severing position, a spacing between the first and second clamping members is smaller than a spacing between the severing member and the first clamping member. Therefore, if tissue is inserted between the two clamping members, it is initially not possible for it to come into contact with the severing member.

To contribute to improved handling of the instrument, the handling device may comprise two actuating members which are movable relative to each other and are coupled with the severing device and the clamping device. The severing device and the clamping device may, therefore, be selectively actuated with the handling device.

The tactility of the instrument may be improved by a first actuating member being rigidly connected to the first clamping member, and by a second actuating member being rigidly connected to the severing member. It is thus possible for an operator to directly introduce a force onto the first and/or the second clamping member and/or the severing member through the actuating members.

The handling device is preferably arranged at a proximal end of the instrument. In particular, the handling device can thus be separated spatially very far from the severing device and the clamping device, which, for example, also enables construction of an endoscopic instrument.

To directly approach an operating site with the clamping device and/or the severing device, it is advantageous for the clamping device and/or the severing device to be arranged at a distal end of the instrument. In particular, the two devices may form a distal end of an endoscopic instrument.

The construction and handling of the instrument are particularly simple when it comprises two rigid arms mounted for pivotal movement on each other, each of the arms having a proximal end and a distal end, when the actuating members are provided at the proximal ends and when the first clamping member and the severing member are respectively provided at one of the distal ends.

A particularly simple construction of the instrument can, in particular, be achieved by the second clamping member being arranged at a distal end of a pivotally mounted lever. This lever does not necessarily have to be directly coupled with an actuating member and may, for example, be mounted in an elastically spring-biased manner relative to the severing member or the first clamping member.

To enable easy and reliable severing of tissue, the severing member advantageously has a cutting edge. It is expedient for the cutting edge to point in the direction of the at least one clamping member.

Furthermore, in accordance with a further preferred embodiment of the invention, an electrical connection device may be provided, which is electrically conductively connected to the at least one clamping member and/or the severing member. The electrical connection device makes it possible in a simple and reliable way to connect the surgical instrument by means of a connecting cable engageable with the connection device to a current source, for example, a high-frequency current generator, so that, as required, a current can be allowed to flow through the at least one clamping member and/or the severing member, for example, to coagulate tissue.

A current source can be connected to the electrical connection device with particular ease when the connection device is arranged in the area of a proximal end of the instrument.

Furthermore, in accordance with a further preferred embodiment of the invention, it may be provided that the electrical connection device has three connecting contacts, a respective one of which is electrically conductively connected to the first clamping member, the second clamping member and the severing member, which are electrically insulated from one another.

The handling of the instrument is further improved when it has an instrument grip which comprises the handling device.

In principle, it is conceivable to fixedly connect the instrument grip permanently to the severing device and/or the clamping device. To make it possible for an operator to use appropriately adapted instrument grips, for example, for left-handed or right-handed persons, it is advantageous for the instrument grip to be releasably connectable to the severing device and/or the clamping device. In addition, such a releasable connectability enables improved cleanability of the instrument.

In principle, it is conceivable to construct the clamping device in the form of a monopolar clamping device. However, for specifically supplying parts of the instrument with current and also prescribing a current flow path, for example, in a patient's body, in a precisely defined manner, it is advantageous for the clamping device to be constructed in the form of a bipolar clamping device.

It may also be advantageous for the severing device to be constructed in the form of a bipolar severing device. A current flow can thus be precisely prescribed in the area of an operating site or, if the instrument is constructed in the form of an endoscopic instrument, also deep inside a patient's body.

FIG. 1 shows a surgical instrument, generally designated by reference numeral 10, in the form of a combination bipolar instrument. It comprises a clamping device 12 formed at a distal end, a severing device 14 also formed at the distal end, and a handling device 16 forming a proximal end of the instrument 10. These will be described in detail hereinbelow.

The instrument 10 comprises two elongated, slightly curved arms 18 and 20, which are of essentially integral construction and are mounted for pivotal movement on each other about a common pivot axis 22. The pivot axis 22 is defined by a longitudinal axis of a bearing sleeve, not shown in greater detail, comprising a sleeve portion with an internal thread, and a head 24 which closes the sleeve portion at one side. Also provided is a joining screw having an external threaded portion, corresponding to the internal thread, with a further head. Head surfaces adjoining the sleeve portion and the external threaded portion extend parallel to each other and face each other when the bearing sleeve is screwed to the joining screw.

The arm 20 is of substantially elongated and bar-shaped construction and of substantially quadrangular cross section. For mounting on the bearing sleeve, it has a transverse bore orientated coaxially with the pivot axis 22. The arm 20 is of overall ridged construction and carries at its distal end a severing member 26 in the form of a cutting tip with a straight-lined cutting edge 28. A proximal end of the severing member 26 is held in a slot 32 extending from a distal end 30 of the arm 20 in proximal direction. The severing member 26 is orientated in such a manner that it defines a plane perpendicular or substantially perpendicular to the pivot axis 22. It is preferably made of an electrically conductive material or has an electrically conductive coating. Adjoining the proximal side of a joining area 34 of the instrument 10, in which the arms 18 and 20 are mounted for pivotal movement relative to each other and on each other about the pivot axis 22, there is an actuating portion 36 which carries a finger ring 38 at its distal end.

A distal end of the arm 18 is constructed as a first clamping member 40 in the form of a clamping jaw with a flat clamping surface 42. The clamping member 40 has a slot-shaped depression 44 extending parallel to a plane through which the pivot axis 22 passes perpendicularly. The depression 44 continues in slot-shaped configuration in proximal direction so as to define a through-opening 50, which is delimited on either side by parallelepipedal bearing arms 46 and 48 and which extends in proximal direction beyond the joining area 34. The through-opening 50 is of such width that the arm 20 rests in the joining area 34 against inner surfaces of the bearing arms 46 and 48 and is guided at these.

At the proximal side of the opening 50, the arm 18 continues in slightly curved configuration, more particularly, away from the arm 20, in proximal direction. The two arms 18 and 20 are of virtually identical construction proximally of the opening 50, i.e., the arm 18 also ends in a finger ring 52. Distally of the finger rings 38 and 52 there is formed a triangular through-opening 54 which decreases in its width and is delimited on either side by two holding bars 56 and 58, which connect the finger rings 38 and 52 to arm portions of the arms 18 and 20, which extend up to the joining area 34.

The instrument 10 further comprises a lever 60 which is also mounted for pivotal movement about the pivot axis 22. At the distal side, the lever 60 is constructed in the form of a second clamping member 62, and, at the proximal side, it extends up to the area of the finger rings 38 and 52. A proximal end area 64 of the lever 60 is constructed in the manner of a grip and has a side surface 66 of undulating design in the direction facing the arm 20 with a curved projection 68, which can nestle in the area of transition 70 of the arm 20 between the finger ring 38 and the bar 58 when the proximal end of the lever 60 is pivoted in the direction towards the arm 20.

At the distal side of the end portion 64, the lever 60 has a through-opening 72 which extends up to the second clamping member 62. The through-opening 72 has a width which corresponds to a spacing between outer side surfaces of the bearing arms 46 and 48, so that bearing arms 74 and 76 laterally delimiting the through-opening 72 rest in the joining area 34 against the bearing arms 46 and 48. In addition, the through-opening 72 is provided in a plane which is orientated perpendicularly to the pivot axis 22.

The second clamping member 62 has a clamping member opening in the form of a through-opening 78 which, as it were, forms a distal end of the through-opening 72. In the area of transition to the second clamping member 62, a width of the through-opening 72 is somewhat reduced, so that, as it were, an optical separation from the through-opening 78 is created. A constriction 80 is thereby defined, at which the through-opening 72 has a minimal width. The length of the through-opening 72 in distal direction is so selected that the distal end 30 of the arm 20 can penetrate the through-opening 72 completely, and the severing member 26 then extends through the constriction 80 in distal direction into the through-opening 78. The constriction 80 thus simultaneously forms a guide for the severing member 26.

Figure 2:
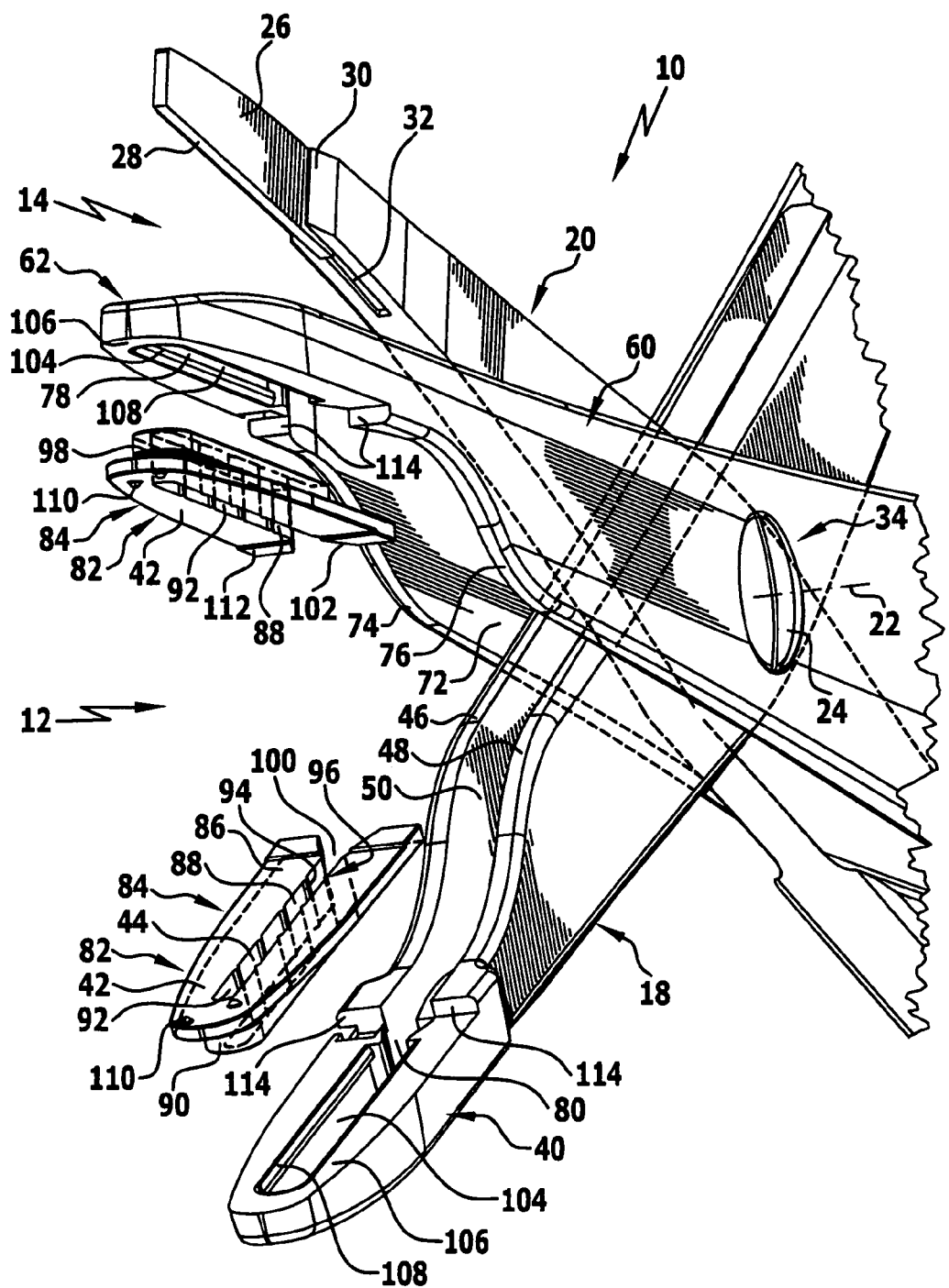
FIG. 2 shows a perspective exploded representation of a distal end of the instrument shown in FIG. 1.
Figure 3:
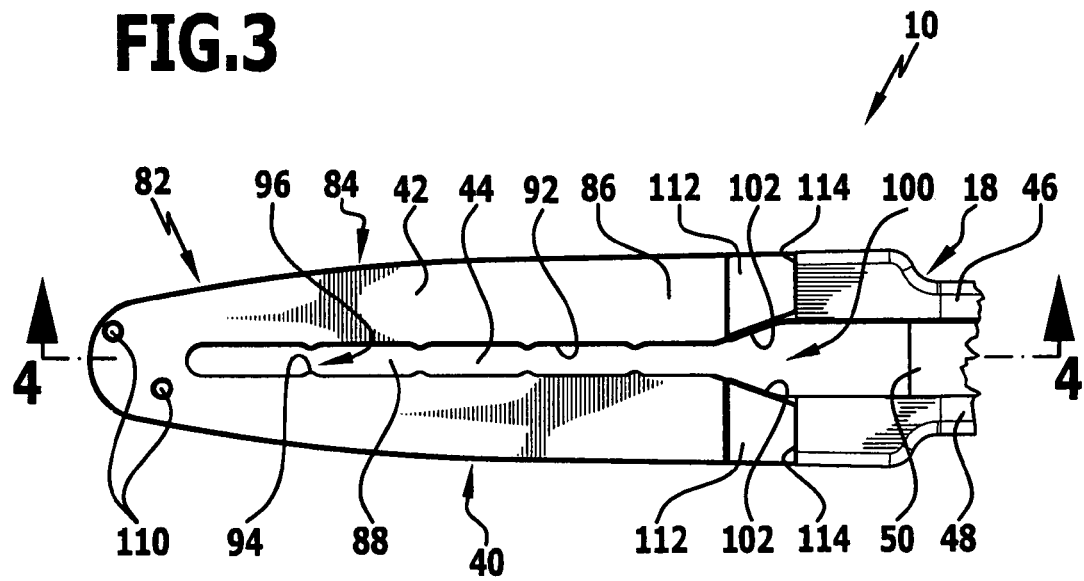
FIG. 3 shows a plan view of a clamping surface of a clamping member of the instrument.
Figure 4:
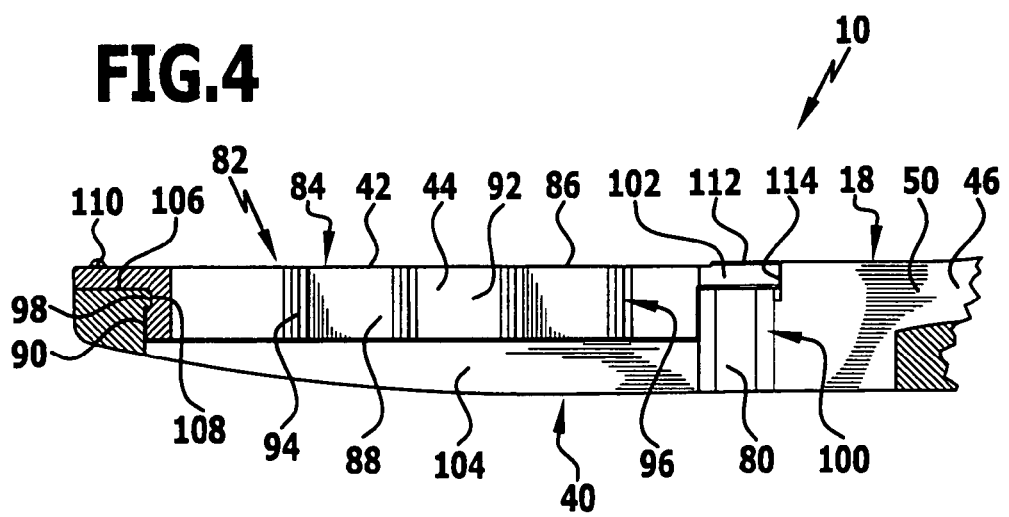
FIG. 4 shows a sectional view taken along line 4-4 in FIG. 3.

The design of the first clamping member 40 will be described in greater detail hereinbelow in conjunction with FIGS. 2 to 4. The design of the first clamping member 40 corresponds substantially to the design of the second clamping member 62 except for the configuration of the clamping member opening, which, in the first clamping member 40, is in the form of the depression 44, in the second clamping member 62 in the form of the through-opening 78. Therefore, the description of the design of the first clamping member 40 will also serve as description of the design of the second clamping member 62.

The first clamping member 40 comprises a severing member guide device 82 in the form of an elongated U-shaped insert 84. The insert 84 comprises a plate-shaped flat section 86 which defines the clamping surface 42. The plate-shaped section 86 comprises a slot 88 open in proximal direction, which also extends further below the section 86 between a U-shaped rim 90 projecting perpendicularly from the section 86. The slot 88 is laterally delimited by mutually opposed side surfaces 92 of the rim 90, which at least partially define the clamping member opening between them. The side surfaces 92 are orientated perpendicularly to the pivot axis 22. Strip-shaped spacer elements 94, arranged parallel and equidistantly in relation to one another, extend over the entire height of the rim 90. The spacer elements 94 projecting from the mutually opposed side surfaces 92 are arranged so as to face one another in pairs and form spacer element pairs 96. The spacer element pairs 96 each form constrictions of the slot 88 and define a minimum width of the slot 88, which has a value which corresponds to a width of the slot 88 between the side surfaces 92 without the spacer elements 94 reduced by twice the height of a single spacer element 94. The spacer elements 94 are fully rounded-off and edge-free.

There is formed immediately below the plate-shaped section 86 on the rim 90 on an outer side thereof a circumferential groove-shaped depression 98. In the area of a proximal end of the insert 84, the slot 88 widens in an end area 100 continuously up to the end, so that two guide surfaces 102 diverging in proximal direction are defined, which are arranged above the constriction 80, which, in the first clamping member 40, too, is formed in the area of transition between the through-opening 50 and the depression 44.

The first clamping member 40 and also the second clamping member 62 have an opening 104 for the insert 84. This is of substantially elongated parallelepipedal shape to enable it to receive the rim 90. Side surfaces 106 of the first clamping member 40 and of the second clamping member 62, which delimit the opening 104, serve as bearing surfaces for the section 86. There is provided immediately below the surface 106 at the opening 104 a half ring-shaped bead 108 which is formed so as to correspond to the depression 98. When, during assembly, the insert 84 is pushed with the rim 90 into the opening 104, the bead 108 locks with the depression 98, so that the insert 84 is held securely in the opening 104. Optionally, the insert 84 may, in addition, be adhesively bonded, soldered or welded.

Distally of the slot 88, there project from the clamping surface 42 two small hemispherical projections 110, which are offset in a longitudinal direction defined by the instrument 10 on either side of the slot 88. The projections 110 are made of an electrically insulating or non-conductive material and ensure that the clamping surfaces 42 of the clamping members 40 and 62 do not come into contact with one another.

The through-opening 78 of the second clamping member 62 is shaped in the same manner as the opening 104 and also has a ring-shaped bead 108. In addition, the distal ends of the arms 18 and 20 have identical dimensions, so that an identical insert 84 for formation of a severing member guide device 82 can be clipped into the through-opening 78 to form the second clamping member 62.

Proximally of the clamping surface 42, the plate-shaped section 86 is somewhat thicker and therefore projects in the form of a flat projection 112 somewhat above the clamping surface 42, as do the projections 110. Proximally, the projections 112 are supported on end surfaces 114 which point in distal direction and are formed by an offset in the area of the clamping members 40 and 62 in the area of transition to the bearing arms 46 and 48 and 74 and 76, respectively.

Preferably, the projections 112 are also electrically nonconductive, as are the projections 110. The clamping surface 42, in turn, is electrically conductive. To this end, a metallic coating may, for example, be applied to the insert 84 which, in particular, may be made of a ceramic material. It is, however, also conceivable to make the ceramic insert 84 electrically conductive in the area of the clamping surface 42 by appropriate doping, so that the severing member guide device 82 can be made entirely of one piece.

An electrical connection device, generally designated by reference numeral 116, is provided at the proximal end area 64 of the lever 60. The connection device 116 comprises three connecting contacts 117 (e.g., receptacles or bores for plug connectors), which can be connected to a connecting cable which serves to supply an electric current, preferably a high-frequency current, from an appropriate current source, for example, a high-frequency generator. In a manner not shown in greater detail, electric wires are led from the connection device 116 through the lever 60, one of which is in electrical contact with the clamping surface 42 of the second clamping member 62. In the joining area 34, electric bushings, electrically insulated from one another, lead to the arms 18 and 20, so that the clamping surface 42 of the first clamping member 40 and also the severing member 26 can be connected in an electrically conductive manner to one of the connecting contacts 117 of the connection device 116. In this way, a bipolar instrument can be constructed for holding and/or severing tissue. For example, the tissue can thus also be coagulated during the holding and/or the severing thereof.

In FIG. 1 the instrument 10 is shown in a cleaning position in which the severing member 26 is completely withdrawn from the clamping member opening in the second clamping member 62. Thus, the two clamping members 40 and 62 and also the severing member 26 can be cleaned in a simple way also during surgery, as all three parts are freely accessible.

In a working position, not shown in greater detail in the Figures, the end portion 64 of the lever is pivoted in the direction towards the finger ring 38 until the projection 68 rests on the area of transition 70. The instrument 10 is so constructed that the cutting edge 28 in this working position does not yet project over the clamping surface 42 of the second clamping member 62. A minimum spacing between the clamping members 40 and 62 is, consequently, determined by a spacing between the clamping surfaces 42 of the clamping members 40 and 62. Owing to its shape, the lever 60 is somewhat elastic and makes it possible, when tissue is clamped between the clamping members 40 and 62, that upon pivoting the proximal end portions of the arms 18 and 20 relative to each other, a portion of the lever 60 extending distally of the pivot axis 22 pivots away from the first clamping member 40, so that the second clamping member 62 releases the cutting edge 28, and this projects beyond the clamping surface 42 of the second clamping member 62. In a severing position, the severing member 26 can be moved with its cutting edge into the depression 44 to sever tissue held between the clamping members 40 and 62.

With their spacer elements 94, the severing member guide devices 82 ensure that the severing member 26 is unable to come into contact with the electrically conductive clamping surfaces 42 of the inserts 84. The spacer elements 94 also ensure that a minimum spacing defined by their height is maintained between the severing member 26 and inner side surfaces 92 of the inserts 84, whereby a minimum spacing of the severing member 26 from the clamping surfaces 42 is maintained at the same time. The spacer elements 94 also serve as guide for the severing member 26, as a distortion of distal portions of the arms 18 and 20 may be caused by the proximal ends of the arms 18 and 20, which form actuating elements, being acted upon with force, with the result that in the worst case the depressions 44 or slots 88 of the clamping members 40 and 62 can no longer be brought into alignment with one another.

The arms 18 and 20 and also the lever 60 may each be made in one piece from a plastic material, but it must be taken into account that electric conductors are also provided in the respective parts, for example, embedded therein by injection molding, so as to enable the severing member 26 and the two clamping surfaces 42 to be electrically conductively connected to the connection device 116.

To form a monopolar instrument, it is, optionally, conceivable to connect only the clamping surface 42 of the first clamping member 40 electrically conductively to the connection device 116. A flow of electric current to bring about coagulation can then be produced with a neutral electrode placed on the patient's body.

The design as a bipolar instrument enables a flow of electric current to be specifically generated between the severing member 26 and the clamping surface 42 of the first clamping member 40 or between the two clamping surfaces 42 of the clamping members 40 and 62.

The invention claimed is:

1. Surgical instrument, comprising:
   a clamping device for holding and/or clamping tissue,
   a severing device for severing tissue,
   a handling device for actuating the clamping device and/or the severing device, the clamping device comprising at least one clamping member having a clamping surface and a clamping member opening,
   the severing device comprising a severing member movable at least partially into the clamping member opening, and
   a severing member guide device comprising an insert adapted to be inserted within the clamping member opening for guiding the severing member in the clamping member opening and for maintaining a spacing from inner side surfaces of the clamping member opening;
   wherein an electrical connection device is provided, which is electrically conductively connected to at least one of the at least one clamping member and the severing member; wherein the electrical connection device has three connecting contacts, a respective one of which is electrically conductively connected to a first clamping member and a second clamping member comprising the at least one clamping member and to the severing member, which are electrically insulated from one another.

2. Surgical instrument in accordance with claim 1, wherein the severing member guide device comprises at least one spacer element which defines a minimum spacing between the severing member and a respective one of the inner side surfaces of the clamping member opening.

3. Surgical instrument in accordance with claim 2, wherein the at least one spacer element is made of an electrically non-conductive material.

4. Surgical instrument in accordance with claim 2, wherein at least one of the severing member guide device and the at least one spacer element is made of a ceramic material.

5. Surgical instrument in accordance with claim 2, wherein the at least one spacer element extends up to the clamping surface.

6. Surgical instrument in accordance with claim 2, wherein two respective spacer elements which are mutually opposed to each other form a spacer element pair.

7. Surgical instrument in accordance with claim 2, wherein a number of the spacer elements are uniformly distributed over the inner side surfaces.

8. Surgical instrument in accordance with claim 2, wherein the spacer elements are of strip-shaped construction.

9. Surgical instrument in accordance with claim 2, wherein the spacer elements extend in a direction transverse or substantially transverse to the clamping surface.

10. Surgical instrument in accordance with claim 1, wherein the severing member guide device comprises at least two spacer elements, each of which define a minimum spacing between the severing member and a respective one of the inner side surfaces of the clamping member opening.

11. Surgical instrument in accordance with claim 10, wherein the at least two spacer elements are associated with the inner side surfaces of the clamping member opening which are mutually opposed.

12. Surgical instrument in accordance with claim 1, wherein the clamping surface is electrically conductive.

13. Surgical instrument in accordance with claim 1, wherein the clamping surface is orientated transversely or substantially transversely to the inner side surfaces of the clamping member opening.

14. Surgical instrument in accordance with claim 1, wherein the severing member guide device is made at least partially of an electrically non-conductive material.

15. Surgical instrument in accordance with claim 1, wherein the severing member guide device is of a one-piece construction.

16. Surgical instrument in accordance with claim 1, wherein the severing member guide device has an opening whose inner side surfaces form, at least in sections, the inner side surfaces of the clamping member opening.

17. Surgical instrument in accordance with claim 1, wherein the severing member guide device has a plate-shaped section with a section surface which forms at least part of the clamping surface of the at least one clamping member.

18. Surgical instrument in accordance with claim 14, wherein the section surface forming at least part of the clamping surface is of an electrically conductive construction.

19. Surgical instrument in accordance with claim 17, wherein the plate-shaped section has a plate opening which forms part of the clamping member opening.

20. Surgical instrument in accordance with claim 19, wherein a rim projecting from the plate-shaped section is arranged so as to surround the plate opening, and an inner surface of the rim forms at least partially the inner side surfaces of the clamping member opening.

21. Surgical instrument in accordance with claim 20, wherein the rim carries at least one spacer element which defines a minimum spacing between the severing member and a respective one of the inner side surfaces of the clamping member opening.

22. Surgical instrument in accordance with claim 21, wherein the spacer element extends over an entire height of the rim.

23. Surgical instrument in accordance with claim 1, wherein the at least one clamping member opening is a depression formed on the clamping member.

24. Surgical instrument in accordance with claim 1, wherein the at least one clamping member opening is a through-opening formed on the clamping member.

25. Surgical instrument in accordance with claim 1, wherein the severing member is at least partially movable through the at least one clamping member opening.

26. Surgical instrument in accordance with claim 1, wherein the at least one clamping member comprises first and second clamping members which are mounted for movement relative to each other.

27. Surgical instrument in accordance with claim 26, wherein the severing device comprises the first clamping member and the severing member, which are movable relative to each other.

28. Surgical instrument in accordance with claim 27, wherein the first clamping member and the severing member are adapted to be brought into contact with each other for severing tissue in a severing position.

29. Surgical instrument in accordance with claim 27, wherein a first actuating member is rigidly connected to the first clamping member, and a second actuating member is rigidly connected to the severing member.

30. Surgical instrument in accordance with claim 26, wherein the second clamping member is arranged at a distal end of a pivotally mounted lever.

31. Surgical instrument in accordance with claim 26, wherein:
in a working position for at least one of clamping, holding, and severing tissue with the instrument, the second clamping member surrounds the severing member at least partially, and
without disassembling the instrument, the severing member and the second clamping member are adapted to be brought into a cleaning position in which the second clamping member completely releases the severing member.

32. Surgical instrument in accordance with claim 31, wherein the second clamping member is movable away from the severing member in a direction towards the first clamping member in order to transfer the instrument from the working position to the cleaning position.

33. Surgical instrument in accordance with claim 31, wherein in the severing position, the severing member projects beyond the second clamping member in a direction towards the first clamping member.

34. Surgical instrument in accordance with claim 31, wherein in any working position with the exception of the severing position, a spacing between the first and second clamping members is smaller than a spacing between the severing member and the first clamping member.

35. Surgical instrument in accordance with claim 26, wherein the first and second clamping members are mounted for pivotal movement relative to each other.

36. Surgical instrument in accordance with claim 1, wherein the severing member and the at least one clamping member are mounted for pivotal movement relative to each other.

37. Surgical instrument in accordance with claim 1, wherein the handling device comprises two actuating members which are movable relative to each other and are coupled with the severing device and the clamping device.

38. Surgical instrument in accordance with claim 37, further comprising two rigid arms mounted for pivotal movement on each other, each of the arms having a proximal end and a distal end, the actuating members being provided at the proximal ends of the arms, and the first clamping member and the severing member being respectively provided at one of the distal ends of the arms.

39. Surgical instrument in accordance with claim 1, wherein the handling device is arranged at a proximal end of the instrument.

40. Surgical instrument in accordance with claim 1, wherein at least one of the clamping device and the severing device is arranged at a distal end of the instrument.

41. Surgical instrument in accordance with claim 1, wherein the severing member has a cutting edge.

42. Surgical instrument in accordance with claim 1, wherein the electrical connection device is arranged in an area of a proximal end of the instrument.

43. Surgical instrument in accordance with claim 1, further comprising an instrument grip which comprises the handling device.

44. Surgical instrument in accordance with claim 43, wherein the instrument grip is releasably connectable to at least one of the severing device and the clamping device.

45. Surgical instrument in accordance with claim 1, wherein the clamping device is constructed in the form of a bipolar clamping device.

46. Surgical instrument in accordance with claim 1, wherein the severing device is constructed in the form of a bipolar severing device.

* * * * *